United States Patent [19]

Hatsuno et al.

[11] 3,930,492

[45] Jan. 6, 1976

[54] AIR-NONCONTACT TYPE BLOOD SAMPLING ASSEMBLY

[75] Inventors: Norio Hatsuno; Tooru Sekiguchi, both of Tokyo, Japan

[73] Assignee: Jintan Terumo Company, Ltd., Tokyo, Japan

[22] Filed: Aug. 21, 1974

[21] Appl. No.: 499,219

[52] U.S. Cl........... 128/2 F; 128/DIG. 5; 128/218 P
[51] Int. Cl.² .................... A61B 5/14; A61M 5/315
[58] Field of Search.... 128/2 F, DIG. 5, 276, 218 P, 128/218 C, 218 M, 218 D, 218 DA, 220

[56] References Cited
UNITED STATES PATENTS

| | | | |
|---|---|---|---|
| 1,718,605 | 6/1929 | Smith | 128/218 D |
| 2,745,403 | 5/1956 | Goldberg | 128/218 D |
| 2,869,541 | 1/1959 | Helmer et al. | 128/218 C |
| 3,200,813 | 8/1965 | Christakis | 128/DIG. 5 |
| 3,336,924 | 8/1967 | Sarnoff et al. | 128/272 |
| 3,527,216 | 9/1970 | Snyder | 128/220 X |
| 3,753,432 | 8/1973 | Guerra | 128/2 F |

FOREIGN PATENTS OR APPLICATIONS 870,669  6/1961  United Kingdom.................. 128/220

*Primary Examiner*—Robert W. Michell
*Assistant Examiner*—Henry J. Recla
*Attorney, Agent, or Firm*—Kemon, Palmer & Estabrook

[57] ABSTRACT

An air-noncontact type blood sampling assembly has a blood sampling container consisting of a tubular body having at one end an elastomeric stopper sealed by a sealing member and opened at the other end and a columnar gasket having a plunger at the rear portion and slidable within said tubular body, and a cylindrical transparent holder having a piercing needle at the forward end adapted to have said sampling container inserted thereinto. Said blood sampling container is previously charged with a larger amount of blood anticoagulant than required.

5 Claims, 4 Drawing Figures

AIR-NONCONTACT TYPE BLOOD SAMPLING ASSEMBLY

This invention relates to a blood sampling assembly for sampling blood without contact with air.

For the purpose of having the knowledge of the condition of the pneumatic function and electrolyte metabolism of a human body, measurement is made of the respective amounts of oxygen and carbon dioxide contained in the arterial blood, or of oxygen saturation or pH of the arterial blood, or quantitative analysis is made of electrolyte components ($Na^+$, $K^+$, $Cl^-$, $HCO_3^-$ and the like) in blood. In such a blood test, contact of a blood sample to be tested with the air or incorporation of the air with the blood sample has an undesirable effect upon a measured value, failing to obtain exact information of such blood sample. It is when blood sampling is carried out that there is particularly a great possibility of air-contact or -incorporation affecting the measurement results.

A customarily prevailing blood sampling method is based on the utilization of an injection syringe. That is to say, liquid paraffin is sucked into a sterilized injection syringe, thereby introducing the liquid paraffin into the contacting section of the plunger of the syringe with the inner wall of the syringe body, and the introduced liquid paraffin is exhausted, thereby extruding the interior air. Then, after sucking of a necessary amount of blood anticoagulant, for example, heparin into the syringe, the syringe needle is pierced into the arterial blood vessel of a patient for performing blood sampling. It is said that where blood sampling is carried out while the piston of the syringe is being pulled, air-cell introduction or hemolysis is likely to take place. Accordingly, blood sampling is conducted by causing blood to be entered into the syringe by blood pressure. After sampling of blood, mercury is further sucked into the syringe, which is fully shaken for mixing the sampled blood with the heparin or for mixing plasma with hematocyte in a separated state. After completion of such series of operations, the sampled blood is subjected to testing. However, the above-mentioned blood sampling method requires many steps and is troublesome. Therefore, there is a great possibility of the air being incorporated with the blood sample unless much attention is paid. Further, the extrusion of the interior air using the liquid paraffin often is not carried out as desired. Furthermore, after sampling of blood, the plunger of the syringe is often carelessly pulled to cause the air to enter the interior of the syringe. Accordingly, the results of one blood test are low in reliability.

A blood collecting assembly using an evacuated tube is also known, which however is unsuitable to sample blood for intrablood gas analysis. The reason is that it never happens that no air is present within the evacuated tube, or that entry of blood into said tube gives rise to the separation of intrablood gases or the hemolysis because the tube interior is in a pressure-reduced state.

Accordingly, an object of the invention is to provide a blood sampling assembly capable of simplifying the blood sampling operations and effecting blood sampling without contact with air.

Another object of the invention is to provide a blood sampling assembly capable of preventing air from being incorporated with the sampled blood even if freely carried after blood is sampled.

These and other objects have been attained by an air-noncontact type blood sampling assembly comprising the combination of: a sampling container including a tubular body opened at both ends and having a circumferential rib in the proximity of its forward end, a needle-pierceable elastomeric stopper sealing the forward end opening section of said tubular body, a columnar gasket having two projections one of which is formed on the outer circumference of its forward end and the other of which is formed on the outer circumference spaced therefrom and slidable within said tubular body due to the action of the arterial blood pressure, and a plunger extending beyond the tubular body from the rearward end portion of the gasket, the outer diameter of said two projections being slightly larger than the inner diameter of said tubular body and said elastomeric stopper being hermetically inserted into the forward end opening section of the tubular body with the partial circumference of the stopper and the forward end opening section of the tubular body including said rib entirely covered with a sealing member, and when said plunger is sufficiently forced into the tubular body, a space having a capacity equivalent to a necessary amount of blood anticoagulant being defined by the forward end plane of the gasket, the inner wall of the tubular body and the rear end plane of the elastomeric stopper; a cylindrical transparent holder having an open end and a restricted end having a threaded hole, for allowing said sampling container to be inserted thereinto, the inner diameter of said holder being slightly larger than the outer diameter of said tubular body; and a needle having a hub at its intermediate portion and two piercing ends, screwed into said threaded hole via said hub, wherein said sampling container is previously charged with a larger amount of blood anticoagulant than required; and when the holder is fitted over the sampling container, at least the blade plane of the rearward piercing end of said needle is protruded from the rear end of said stopper so as to exhaust the air within the sampling container therefrom.

This invention can be more fully understood from the following detailed description when taken in conjunction with the accompanying drawing, in which.

Figure 1:
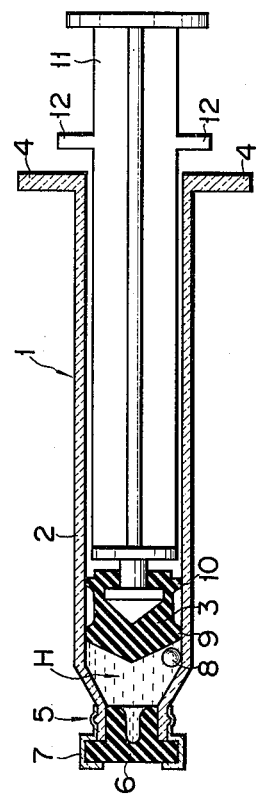
FIG. 1 is a longitudinal sectional view of the blood sampling container of a blood sampling assembly according to the invention.

An embodiment of the invention will hereinafter be described with reference to the accompanying drawing. Throughout the drawing the same parts and sections are denoted by the same reference numerals. FIG. 1 shows the blood sampling container 1 of a blood sampling assembly according to the invention, previously charged with a slightly larger amount of liquid anticoagulant H (for example, heparin) than required. Said sampling container 1 includes a tubular body 2 and a columnar gasket 3 slidable within said tubular body 2. The tubular body 2 has a forward end opening section whose inner diameter is smaller than that of its main body, and the main body is tapered toward the opening section. On the rear end of the tubular body 2 is integrally formed a flange 4 outwardly projecting perpendicularly to the axis of the tubular body 2. In the proximity of the forward end of the tubular body is formed a circumferential annular rib 5.

Figure 4:
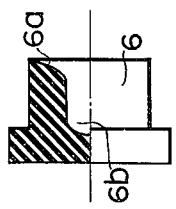
FIG. 4 is a partial cross-sectional view of the rubber plug.

A pierceable elastomeric stopper, for example, a rubber plug 6 is hermetically fitted into the forward end opening section of the tubular body. In FIG. 1, the rubber plug 6 has an enlarged head at the forward end, and when the piercing needle is pierced into the rubber plug, said enlarged head prevents the rubber plug from being forcibly inserted into the interior of the tubular body any further. The inner wall 6a of the rubber plug 6 is formed at its center into a shape conically hollowed toward the interior thereof so as to enable, when the sampling container has been made vertical, air bubbles to be collected into said hollowed section. Further, the inner wall 6a is formed at its center with a concave section 6b so as to enable said air bubbles to be further collected thereinto and simultaneously to receive therein the blade end of the piercing needle 14 pierceable into the rubber plug 6 (see FIG. 4). The enlarged head of the rubber plug and the opening section of the tubular body are entirely covered from outside with a sealing member 7 such as an aluminum sheet or heat-shrinkable plastic tube so as to cause the sealing member to cover the rib 5 of the tubular body, thereby sealing the opening section so as to permit it to be kept in an air-tight condition. The blood sampling container is previously charged with the anticoagulant H and optionally with a ball 8. The ball may be useful for mixing together said anticoagulant and the sample blood, and be of any quality if it is relatively high in density and is incorrodable by the contents (blood and anticoagulant) of the sampling container.

Figure 3:
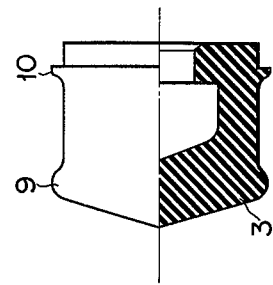
FIG. 3 is a partial cross-sectional view of the gasket.

A columnar gasket 3 is integrally formed with two circumferential projections 9 and 10 whose outer diameters are slightly larger than the inner diameter of the tubular body 2, on the outer circumference of its forward end and on the outer circumference spaced therefrom, respectively, thereby keeping the sampling container in an air-tight condition and simultaneously reducing the friction between the inner wall of the tubular body and the gasket, resultantly to render the gasket slidable within the tubular body due to the action of the arterial blood pressure. To explain a concrete example illustrated in the drawing, as shown in FIG. 3, the projection 9 on the forward end side is so formed as to have a semicircular cross section, and the projection 10 on the rearward end side is formed such that the wall plane thereof at the rearward end side is formed vertical and simultaneously the wall plane at the forward end side is formed oblique in a circularly expanded manner. Formation of the projection 10 in such manner enables the projection 10 to be prevented to a maximum extent from being bent when the gasket is moved in a rearwardly direction while slidably contacting the inner wall of the tubular body 2. That is, movement of the gasket due to the action of the arterial blood pressure and yet maintenance of the adherence of the gasket to the inner wall of the tubular body 2 are possible. However, the foregoing is only an example, and this invention can be practiced even when the wall plane of the projection 10 is formed vertical on the forward end side and oblique on the rearward end side.

For the purpose of making the gasket 3 within the tubular body 2 smoothly slidable, a lubricant, for example, a silicone having a relatively high viscosity is coated on the inner wall of the tubular body 2. The viscosity of a silicone used is, for example, 30,000 c.s. Application of a silicone having such relatively high viscosity facilitates commencement of the gasket movement. It is to be noted that if coating of said silicone is performed excluding the inner wall of the tubular body portion filled with heparin, adherence of air bubbles to said inner wall will be prevented to a maximum extent even when such air bubbles have entered the sampling container 1.

Detachably attached to the rear portion of the gasket is a plunger 11, on the outer circumference of which is integrally formed, according to FIG. 1, a stopper 12 engageable with the flange 4 of the tubular body. The position of said stopper is determined so as to prevent the gasket from being repelled by the tapered section of the tubular body due to the excessive insertion of the plunger into said body. If the positioning of the stopper 12 is effected as such, it will prevent the air from entering into the interior of the blood sampling container via the piercing needle due to said repulsion.

When the plunger 11 has been fully inserted into the tubular body, a space, i.e., the dead space 22 (see FIG. 2) of the sampling container 1 is defined by the forward end plane of the gasket 3, the inner wall of the tubular body and the rear end plane of the rubber plug 6. Said dead space and the interior of the piercing needle 14 have a capacity equivalent to a necessary amount of anticoagulant. The capacity of the dead space 22 is determined depending upon the necessary amount of said anticoagulant considering the interior volume of the piercing needle 14.

Figure 2:
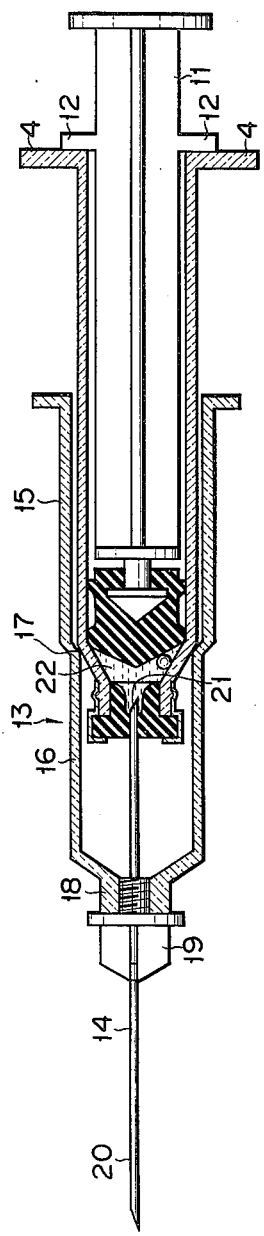
FIG. 2 is a longitudinal sectional view of the blood sampling assembly according to the invention which is kept in a state wherein the sampling container of FIG. 1 is inserted into a holder.

FIG. 2 shows the blood sampling assembly of the invention in which a transparent cylindrical holder 13 is fitted over the above-mentioned sampling container 1 and the plunger 11 is pushed so as to extrude the air which may be present within the sampling container together with the charged anticoagulant via the needle 14, namely the blood sampling assembly immediately before the sampling of blood. The holder 13 has an open end and a restricted end having a threaded hole. According to FIG. 2, the holder 13 consists of a rearward part 15 whose inner diameter is slightly larger than the outer diameter of the tubular body 2 of the sampling container and a forward part 16 whose inner diameter is smaller than that of said rearward part and slightly larger than the outer diameter of the enlarged head of the rubber plug 6, and a tapered section is formed which begins from said rearward part and ends at said forward part. When the holder has been fitted over the tubular body, the terminating point 17 of said tapered section engages the tapered plane of the tubular body. In this case, the tapered plane of the holder may hermetically be contacted with that of the tubular body.

The forward part 16 of the holder has a cylindrical head 18 whose diameter is smaller than that of said forward part. Into said head 18 is screwed via a hub 19 the needle 14 having its piercing ends 20 and 21. The length of the needle which falls within the tubular body is so determined that when the holder has been fitted over the sampling container, the piercing end 21 of the needle is thrust into the rubber plug 6 and at least the blade plane of the needle protruds from the rear end plane of the rubber plug. An excessive protrusion of said protruded portion of the needle renders it difficult to extrude the air from the interiors of the needle and sampling container.

When the holder 13 is fitted over the sampling container 1 and the plunger 11 is pushed to extrude the anticoagulant via the needle, the air within the sampling container is extruded to cause the dead space 22 to be filled with a necessary amount of the anticoagulant. In FIG. 2 this condition is shown.

When the blood sampling assembly maintained in this condition is thrust into a patient's arterial blood vessel, the blood is gradually introduced into the interior of the tubular body due to the action of the blood pressure. After completion of sampling a desired amount of blood, the needle is drawn out and thereafter the sampling container is dismembered from the holder and then is sufficiently shaken for mixing the sampled blood with the heparin previously charged as the anticoagulant. At this time, the ball contributes to the promotion of said mixing. The hole created by thrusting the needle into the rubber plug of the sampling container is closed by the elasticity of rubber to cause the charged mass to be fully shielded from the ambient air, enabling the sampling container to be freely carried over to any desired place with no room for entry of the air into the sampling container left.

Where the intrablood gas analysis is performed, a piercing needle provided with an adaptor adapted for the sample inlet of a gas analysis device is screwed into the holder, and the plunger is pushed to introduce the sampled blood into the gas analysis device.

As above described, the blood sampling assembly of the invention enables the sampling operations to be readily carried out and the blood sampling to be effected without any possibility of the air being incorporated with the sampled blood, and eliminates the necessity of using the mercury harmful to a human body for mixing the sampled blood with the anticoagulant, said mercury having been used in conventionally effecting blood sampling by a syringe. Further, the maintenance or conveyance of the sampled blood can be readily effected without any possibility of the air being incorporated with the sampled blood. Thus, the blood sampling assembly of the invention is extremely practical from the medical point of view.

What we claim is:

1. An air-noncontact type blood sampling assembly for collecting arterial blood directly from an arterial blood vessel through a needle without entrainment of ambient air which comprises in combination:
    A. a sampling container for containing arterial blood including:
        a. a tubular body having forward and rearward open ends and having a small circumferential rib adjacent the forward end,
        b. a needle-pierceable elastomeric stopper hermetically inserted into and sealing the forward end opening section of said tubular body, the partial circumferences of the stopper and the forward end section of said tubular body including said rib being covered with a sealing member hermetically sealing the stopper to said tubular body,
        c. a columnar gasket disposed within said tubular body and having means for slidable, air tight movement in said tubular body due to arterial blood pressure, wherein said means includes a first circumferential projection near its forward end and a second circumferential projection spaced apart therefrom, the outer diameter of the two projections being slightly larger than the inner diameter of said tubular body thereby the gasket may slidably air-tightly move in said tubular body due to arterial blood pressure, the forward end plane of the gasket in its most forward position within the tubular body, the inner wall of said tubular body and rear end plane of said stopper defining a space having a capacity equivalent to a predetermined amount of blood anticoagulant,
        d. blood anticoagulant in an amount slightly larger than said predetermined amount contained in said tubular body between said stopper and said gasket; and
        e. a plunger fixedly secured to said gasket;
    B. a cylindrical transparent holder having an open rear end and a restricted forward end comprising a threaded hole, embracing said sampling container, the inner diameter of said holder being slightly larger than the outer diameter of said tubular body of said sampling container, and;
    C. a needle having a forward end portion and a rearward end portion integrally joined by an intermediate portion, piercing ends on said forward and rearward portions, a hub on said intermediate portion, said hub being screwed into said threaded hole in said holder, said rearward portion being of such length that at least the blade plane of the piercing end of said rearward portion will protrude from the rear end of said stopper when the sampling container is moved to its most forward position within said holder.

2. A blood sampling assembly according to claim 1 wherein a ball suitable for mixing arterial blood with the blood anticoagulant is contained in said tubular body between said stopper and said gasket.

3. A blood sampling assembly according to claim 1, wherein said stopper in the sampling container has its rear end plane concaved.

4. A blood sampling assembly according to claim 1 wherein said first circumferential projection on said gasket is formed with a semicircular cross section and said second circumferential projection is formed with a rearward end side square to the longitudinal axis of said gasket and with a forward end side that is oblique to said axis in a circularly expanded manner.

5. A blood sampling assembly according to claim 1, wherein the inner surface of said tubular body has a coating of silicone lubricant thereon to assist the movement of said gasket under influence of arterial blood pressure.

* * * * *